United States Patent
Biondo et al.

(10) Patent No.: US 8,196,694 B2
(45) Date of Patent: Jun. 12, 2012

(54) VEHICLE IMMOBILIZER METHODS AND APPARATUS BASED ON DRIVER IMPAIRMENT

(75) Inventors: William A. Biondo, Beverly Hills, MI (US); Clark E. McCall, Ann Arbor, MI (US); David T. Proefke, Madison Heights, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 37 days.

(21) Appl. No.: 12/470,313

(22) Filed: May 21, 2009

(65) Prior Publication Data

US 2010/0294583 A1 Nov. 25, 2010

(51) Int. Cl.
*B60K 28/06* (2006.01)
(52) U.S. Cl. .......................... 180/272; 180/271; 701/45
(58) Field of Classification Search .................. 180/271, 180/287, 272; 74/473.1, 473.21; 701/45, 701/48, 51, 53, 62
See application file for complete search history.

(56) References Cited

U.S. PATENT DOCUMENTS

| | | | | | |
|---|---|---|---|---|---|
| 3,831,707 | A | * | 8/1974 | Takeuchi | 180/272 |
| 5,531,225 | A | * | 7/1996 | Nawata et al. | 600/532 |
| 6,967,581 | B2 | * | 11/2005 | Karsten | 340/576 |
| 7,796,021 | B2 | * | 9/2010 | Saban | 340/438 |
| 2005/0021190 | A1 | * | 1/2005 | Worrell et al. | 701/1 |
| 2006/0006990 | A1 | * | 1/2006 | Obradovich | 340/439 |
| 2006/0215884 | A1 | | 9/2006 | Ota | |
| 2007/0120691 | A1 | | 5/2007 | Braun | |
| 2007/0144812 | A1 | * | 6/2007 | Stewart et al. | 180/272 |
| 2008/0223646 | A1 | * | 9/2008 | White et al. | 180/287 |
| 2009/0090577 | A1 | * | 4/2009 | Takahashi et al. | 180/272 |
| 2009/0211831 | A1 | * | 8/2009 | Takamatsu | 180/272 |
| 2009/0259369 | A1 | * | 10/2009 | Saban | 701/45 |
| 2010/0108425 | A1 | * | 5/2010 | Crespo et al. | 180/272 |

FOREIGN PATENT DOCUMENTS

| | | |
|---|---|---|
| DE | 4200642 A1 | 7/1993 |
| DE | 10220782 A1 | 11/2003 |
| DE | 102004005163 B3 | 6/2005 |
| DE | 602006000078 T2 | 5/2008 |
| DE | 102007046037 B3 | 4/2009 |
| JP | 2008302915 A | 12/2008 |

OTHER PUBLICATIONS

German Office Action for German Application 10 2010 020 857.4-21 mailed Nov. 22, 2010.

* cited by examiner

*Primary Examiner* — Eric Culbreth
*Assistant Examiner* — Barry Gooden, Jr.
(74) *Attorney, Agent, or Firm* — Ingrassia Fisher & Lorenz P.C.

(57) ABSTRACT

Embodiments include systems and methods for immobilizing a motor vehicle. A system comprises an impairment sensor system and a control subsystem. The impairment sensor system is adapted to perform an analysis of a sample provided by an operator of a motor vehicle, where the analysis includes determining an impairment-related metric based on the sample. The control subsystem is adapted to control at least one mobility-related apparatus and at least one non-mobility-related apparatus of the motor vehicle. When the result of the analysis indicates that the impairment-related metric does not meet a criteria, the control subsystem is adapted to control the at least one mobility-related apparatus in a manner that disables the motor vehicle from moving and to control the at least one non-mobility-related apparatus in a manner that allows the at least one non-mobility-related apparatus to operate.

20 Claims, 4 Drawing Sheets

VEHICLE IMMOBILIZER METHODS AND APPARATUS BASED ON DRIVER IMPAIRMENT

TECHNICAL FIELD

Embodiments relate to methods and apparatus for immobilizing a vehicle based on potential driver impairment, and more particularly to methods and apparatus for immobilizing a vehicle based on blood alcohol determinations.

BACKGROUND

As a penalty for drivers convicted of driving under the influence of alcohol, many municipalities require by law that an ignition interlock device (or an "alcohol ignition interlock device") be installed in the driver's vehicle. An ignition interlock device is a mechanism adapted to determine a blood alcohol concentration, typically through the analysis of the driver's breath. Typically, an ignition interlock device is installed on a motor vehicle's dashboard. Before the vehicle's motor can be started, the vehicle operator (e.g., the driver) must exhale into the device. The device then determines a blood alcohol concentration, and when the analyzed blood alcohol concentration corresponds to a concentration that exceeds a predefined threshold (e.g., 0.02 to 0.04 percent), the device interrupts the vehicle's ignition system. Accordingly, the vehicle's motor or engine is disabled from starting.

Although current ignition interlock devices have increased public safety from the standpoint of keeping impaired drivers off the road, there are some situations in which the use of such systems may pose a hazard to the vehicle operator. For example, when an ignition interlock device prohibits a vehicle from starting, an impaired person may decide to remain in the vehicle for shelter or a place to rest. If the vehicle is located in an extremely cold or an extremely hot environment, this may pose a health risk to the person. Accordingly, what are needed are systems and methods that increase the safety to the vehicle operator at times when the vehicle is immobilized. Other desirable features and characteristics will become apparent from the subsequent detailed description and the appended claims, taken in conjunction with the accompanying drawings and the foregoing technical field and background.

SUMMARY

An embodiment includes a system comprising an impairment sensor system and a control subsystem. The impairment sensor system is adapted to perform an analysis of a sample provided by an operator of a motor vehicle, where the analysis includes determining an impairment-related metric based on the sample. The control subsystem, which is operatively coupled with the impairment sensor system, is adapted to control at least one mobility-related apparatus and at least one non-mobility-related apparatus of the motor vehicle. When the result of the analysis indicates that the impairment-related metric does not meet a criteria, the control subsystem is adapted to control the at least one mobility-related apparatus in a manner that disables the motor vehicle from moving and to control the at least one non-mobility-related apparatus in a manner that allows the at least one non-mobility-related apparatus to operate.

Another embodiment of a system comprises an impairment sensor system. The impairment sensor system is adapted to provide a signal, when the impairment sensor system detects an impairment-related metric that does not meet a criteria, that causes at least one mobility-related apparatus of a motor vehicle to be controlled in a manner such that the motor vehicle is disabled from moving. The signal also causes at least one non-mobility-related apparatus to be controlled in a manner that allows the at least one non-mobility-related apparatus to operate.

Another embodiment includes a method for immobilizing a motor vehicle. The method comprises the steps of determining an impairment-related metric from a sample obtained from a vehicle operator, and determining whether the impairment-related metric meets a criteria. When the impairment-related metric does not meet the criteria, the method further comprises disabling at least one mobility-related apparatus of the motor vehicle in order to disable the motor vehicle from moving, while refraining from disabling non-mobility-related apparatus of the motor vehicle.

BRIEF DESCRIPTION OF THE DRAWINGS

Embodiments of the inventive subject matter will hereinafter be described in conjunction with the following drawing figures, wherein like numerals denote like elements.

DETAILED DESCRIPTION

The following detailed description is merely exemplary in nature and is not intended to limit the scope or the application and uses of the inventive subject matter. Furthermore, there is no intention to be bound by any expressed or implied theory presented in the preceding technical field, background, summary or the following detailed description. In the following description, like reference numbers relate to like elements in each of the Figures.

Embodiments include methods and apparatus for immobilizing a vehicle based on determinations of potential driver impairment. As used herein, the term "impairment" or "impaired" may refer to one or more driver characteristics that may detrimentally affect a driver's ability safely to operate a motor vehicle. For example, but not by way of limitation, "impairment" may include alcohol-related impairment, prescription or illegal drug-related impairment, impairment caused by neglecting to take medications, fatigue-related impairment, physical disability related impairment, and so on. Although embodiments described herein may discuss alcohol-related impairment in more detail, it is to be understood that other embodiments include methods and apparatus for immobilizing a vehicle based on determinations of other types of driver impairment. Accordingly, such alternate embodiments are intended to be included within the scope of the inventive subject matter.

As discussed previously, a traditional ignition interlock device causes operation of a vehicle's engine or motor to be inhibited when the device detects a blood alcohol level above a threshold. Unlike these traditional systems, embodiments of the inventive subject matter allow certain of the vehicle's subsystems to be activated while restricting vehicle mobility, even when a blood alcohol level above a threshold is detected. For example, the vehicle's heating, ventilation, and air conditioning (HVAC) system may remain enabled, even when vehicle mobility is disabled. This may have the advantageous result of increasing driver safety, particularly when the vehicle is located in an area of extreme temperatures.

Figure 1:
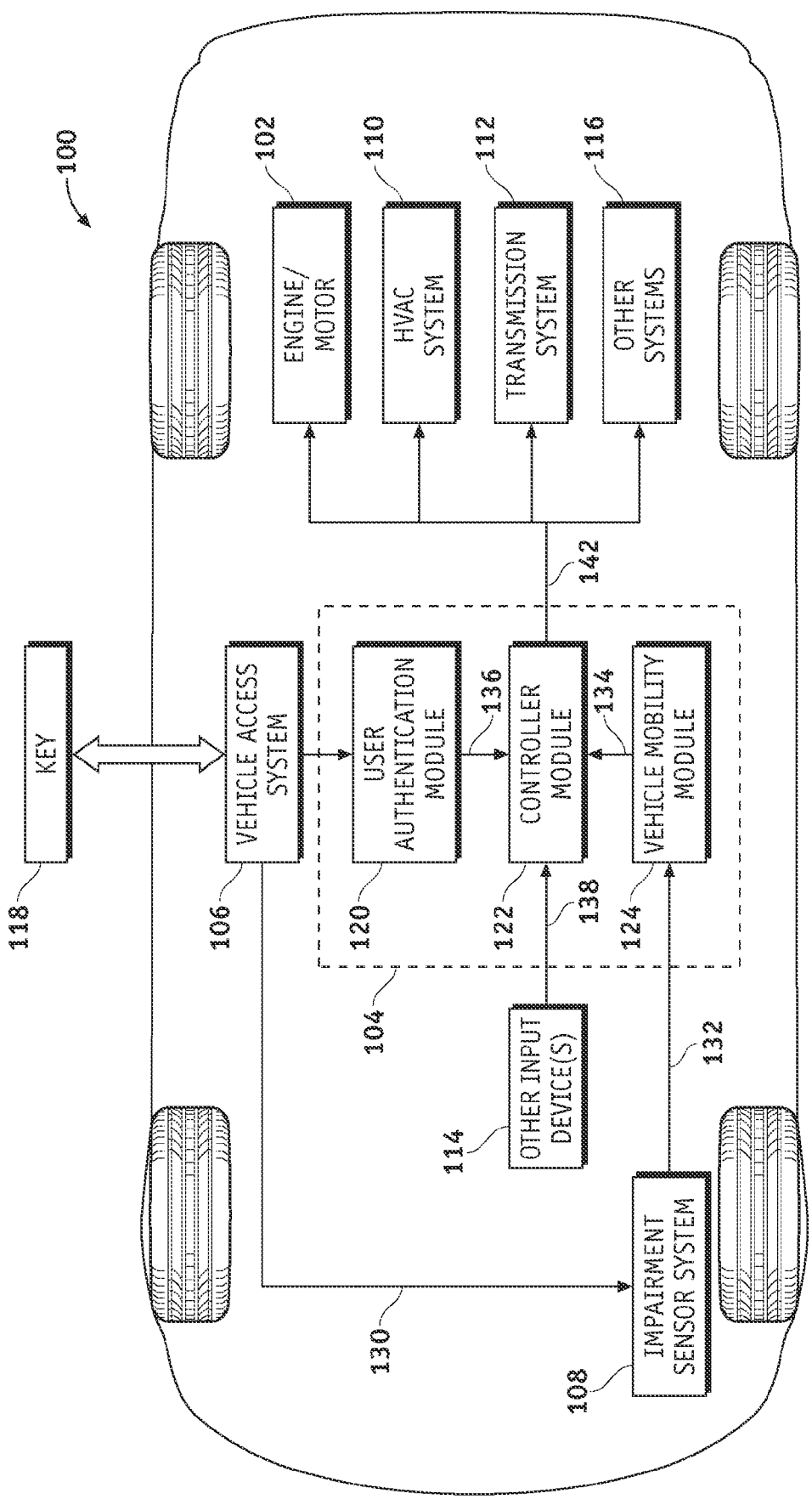
FIG. 1 is a simplified block diagram of a system adapted to control vehicle mobility based on driver impairment determinations, in accordance with an embodiment.

FIG. 1 is a simplified block diagram of a system 100 adapted to control vehicle mobility based on driver impairment determinations, in accordance with an embodiment. According to an embodiment, system 100 is incorporated into a motor vehicle. A motor vehicle into which system 100 may be incorporated may be any one of a number of different types of motor vehicles, including, for example, a conventional type of motor vehicle that includes an internal combustion engine (e.g., a gasoline or diesel fueled combustion engine, a gasoline/alcohol ("flex fuel") combustion engine, or a gaseous compound (e.g., hydrogen and natural gas) fueled engine), a hybrid-electric vehicle (e.g., a vehicle that includes an internal combustion engine and an electric motor to provide propulsion), or an all-electric vehicle (e.g., a vehicle that includes only an electric motor to provide propulsion).

System 100 includes an internal combustion engine and/or electric motor 102 (depending on the type of motor vehicle), processing and control subsystem 104, vehicle access system 106, impairment sensor system 108, HVAC system 110, and key 118. In a vehicle that includes an internal combustion engine, system 100 also includes a throttle (not illustrated) and transmission system 112. According to various embodiments, system 100 also may include one or more other input devices 114 and/or various other systems 116, as will be discussed in more detail later.

According to an embodiment, impairment sensor system 108 includes an analyzer adapted to estimate an impairment-related metric ("IRM") (e.g., blood alcohol content) from a non-invasive interaction with a vehicle operator (e.g., from a breath sample). The analyzer may include, for example, an ethanol-specific fuel cell sensor, which generates an electric current having a magnitude that is related to a concentration of alcohol within a breath sample. Alternatively, the analyzer may utilize infrared spectroscopy or other technologies for detecting a concentration of alcohol from transdermal images. From the detected alcohol concentration, the impairment sensor system 108 may determine a detected blood alcohol concentration. According to an embodiment, the analyzer is located in proximity to the driver's seat of the vehicle (e.g., attached to the dashboard), and is operatively coupled with other components of the system 100, as illustrated in FIG. 1. According to other embodiments, impairment sensor system 108 may include apparatus adapted to estimate IRMs other than blood alcohol content. For example, impairment sensor system 108 may include apparatus adapted to estimate eye nystagmus or blink rate, which metrics may be relevant to a determination of driver fatigue or potential impairment. According to still other embodiments, impairment sensor system 108 may include apparatus adapted to prompt the driver to perform logical tasks (e.g., answer questions) or physical tasks, and to produce an IRM related to the accuracy of the driver's performance.

Along with the analyzer, impairment sensor system 108 may include a user interface (not illustrated), which is adapted to provide an indication to the vehicle operator when a sample is required. As used herein, the term "sample" may include a biological sample (e.g., breath, blood), an optical sample (e.g., an eye scan), or a user input (e.g., an answer to a system-provided question or request for driver action), among other things. For example, the system 100 may require a breath sample when the vehicle operator is present in the driver's seat, and attempts to start the engine/motor 102 of the vehicle (e.g., using wireless key 118 or another key, as will be described later). In alternate embodiments, the system 100 may require the driver to position his or her eyes in alignment with or proximity to an optical sensor that may sense eye nystagmus or blink rate. In still other alternate embodiments, the system 100 may require the driver to touch a sensor to allow for a non-invasive blood evaluation. In still other alternate embodiments, the system 100 may require the driver to answer a question or to perform a physical task. Vehicle access system 106 may provide a signal 130 to impairment sensor system 108 when such an attempt is made, as will be described in detail later. In addition to an initial sample, the system 100 may require additional samples at random times while the vehicle is being driven.

According to an embodiment, when the impairment sensor system 108 detects an IRM (e.g., a blood alcohol concentration) that does not satisfy a criteria (e.g., the blood alcohol concentration is above a predefined threshold), the system 100 may cause the vehicle to be immobilized while allowing some subsystems of the vehicle to operate (e.g., engine/motor 102, HVAC system 110, and other systems 116). According to an embodiment, upon receiving and analyzing the sample, impairment sensor system 108 provides a signal 132 to processing and control subsystem 104, which indicates the results of the analysis. According to various embodiments, the result-conveying signal 132 may indicate a "pass" or a "fail," or may include a value indicating the detected IRM (e.g., a blood alcohol concentration). According to another embodiment, the signal 132 may indicate an operational "mode" that the vehicle may enter, which is dependent upon the results of the IRM (e.g., breath alcohol) analysis. The various operational modes will be described in more detail below. According to another embodiment, information within the signal 132 may be encrypted, encoded, or hashed, or other security measures may be applied to the signal 132 in order to deter manipulation aimed at disabling or circumventing the system.

Processing and control subsystem 104 may include one or more automotive control modules, electronic control units, general-purpose and/or special-purpose processors, and/or associated electronics. In general, processing and control subsystem 104 is adapted to receive information from various sources (e.g., vehicle access system 106, impairment sensor system 108, and other input devices 114), and to control the operation of the vehicle based on the received information. According to an embodiment, processing and control subsystem 104 includes a user authentication module 120, a controller module 122, and a vehicle mobility module 124. Each of these modules 120, 122, 124 may be implemented using separate hardware, or some or all of the modules may be integrated into the same hardware. FIG. 1 depicts these modules 120, 122, 124 as separate entities for explanation purposes, and not for limitation purposes. The functionality of each module 120, 122, 124 will be described in more detail below.

Vehicle mobility module 124 receives the result-conveying signal 132 from impairment sensor system 108. Based on the signal 132, vehicle mobility module 124 authorizes entry into one of a plurality of operational modes, according to an embodiment, by sending an operational mode signal 134 to controller module 122. For example, the operational modes may include a "full operational mode", a "no-mobility operational mode", and a "non-operational mode," according to an embodiment. The full operational mode may be authorized, for example, when the signal 132 from impairment sensor system 108 indicates that the IRM satisfies criteria representative of a lack of driver impairment (e.g., a blood alcohol concentration is below a predefined threshold). In the full operational mode, all of the vehicle subsystems (e.g., engine/motor 102, HVAC system 110, transmission system 112, and other systems 116) are enabled, and the vehicle is capable of being mobilized based on operator inputs. In contrast, the no-mobility operational mode may be requested when the signal 132 from impairment sensor system 108 indicates that the IRM does not satisfy criteria representative of a lack of driver impairment, or the IRM satisfies criteria representative of driver impairment (e.g., a blood alcohol concentration is above a predefined threshold). In the no-mobility operational mode, only some of the vehicle subsystems are enabled, and other systems that enable the vehicle to be mobilized are disabled, according to an embodiment. The non-operational mode may be entered, for example, when the controller module 122 fails to receive an authentication signal 136 from user authentication module 120. More particularly, in the no-mobility operational mode, one or more "mobility-related apparatus" of the vehicle are controlled or disabled, and one or more "non-mobility-related apparatus" of the vehicle are enabled. As used herein, a "mobility-related apparatus" includes an apparatus selected from a group of apparatus that includes, but is not limited to, a shift control mechanism, a throttle, a transmission system (e.g., transmission system 112), a fuel delivery system, propulsion battery energy, and an electric park brake system. A "non-mobility-related apparatus" includes an apparatus selected from a group of apparatus that includes, but is not limited to an engine, a motor (e.g., engine/motor 102), an HVAC system (e.g., HVAC system 110), an entertainment system (e.g., a radio, a digital audio player, or a video player), a window actuator, and a door lock actuator. The vehicle access system 106 and the user authentication module 120 will now be discussed, prior to discussing how controller module 122 implements the various operational modes.

Vehicle access system 106 may be implemented as a wireless access system, an electronically controlled access system, or a traditional mechanical system. According to an embodiment, vehicle access system 106 is adapted to initiate the process of turning the vehicle on and off. When vehicle access system 106 is implemented as a wireless access system, vehicle access system 106 initiates turning the engine/motor 102 on or off in response to radio frequency (RF) signals produced by wireless key 118. Each RF signal transmitted by wireless key 118 may include an encrypted, unique digital code and an encoded command (e.g., "unlock", "lock", "vehicle start," "vehicle stop"). For example, when a vehicle operator presses a "vehicle start" button on wireless key 118, the wireless key 118 transmits an RF signal that includes the encrypted, unique digital code and an encoded version of a "vehicle start" command. Alternatively, for a proximity-type key, vehicle access system 106 may initiate turning the vehicle on or off in response to its detecting that the key is in proximity to the vehicle (or in the interior cab), receiving an RF signal from the wireless key 118 with the encrypted, unique digital code, and also detecting that the operator has actuated a "start" or "on" control within the vehicle (e.g., on or near the steering column). When vehicle access system 106 is implemented as an electronically controlled access system, vehicle access system 106 may initiate turning the vehicle on or off in response to its detecting that the electronic key has been inserted into a key receptacle (e.g., on or near the steering column), and receiving a signal from the electronic key with the encrypted, unique digital code.

Either way, the vehicle access system 106 receives and decrypts the unique digital code, and may send the decrypted digital code and the command to user authentication module 120. In an alternate embodiment, the vehicle access system 106 may send the encrypted digital code and the command to user authentication module 120, which performs the decryption process. User authentication module 120 determines whether or not the digital code corresponds to a digital code for an authorized key. When it does, the user authentication module 120 or the vehicle access system 106 may send a signal to controller module 122, which indicates that vehicle operation is authorized. According to an alternate embodiment, when vehicle access system 106 is implemented as a traditional mechanical system, the operator inserts a mechanical key into a key receptacle (e.g., on or near the steering column), and turns the key. When the key turns, the vehicle access system 106 may send a signal to controller module 122, which indicates that vehicle start is authorized.

According to an embodiment, the vehicle access system 106 supports "remote vehicle start" and "remote vehicle stop" functions. Accordingly, even when the wireless key 118 is not located within the interior cab, depression of the "vehicle start" button may initiate the process of starting the vehicle. According to an embodiment, and as will be described in more detail below, when a remote vehicle start is requested (e.g., by an authorized wireless key 118), the system 100 enters a no-mobility operational mode. The system 100 then remains in the no-mobility operational mode until the operator enters the vehicle and provides a sample to the impairment sensor system 108, according to an embodiment. If the impairment sensor system 108 determines that an IRM determined from the sample meets a criteria (e.g., the operator's blood alcohol concentration level is below a predefined threshold), then the system 100 may transition to the full operational mode, as described in more detail below. Otherwise, the system 100 will remain in the no-mobility operational mode until either: 1) the system transitions to a non-operational mode as is common in remote vehicle start implementations; or 2) the system receives a sample from which an IRM is determined that meets a criteria (e.g., the operator's blood alcohol concentration level is below a predefined threshold), at which time the system may transition to the full operational mode.

As mentioned previously, controller module 122 implements a full operational mode, a no-mobility operational mode, or a non-operational mode based on signals 134, 136 received from vehicle mobility module 124 and user authentication module 120, respectively. More particularly, controller module 122 enters or remains in a non-operational mode unless and until controller module 122 receives an authentication signal 136 from user authentication module 120, which indicates that an operator with an authorized key has requested that the vehicle be started. In the non-operational mode, neither the engine/motor 102, the HVAC system 110, the transmission system 112, nor other systems 116 of the vehicle are placed in an operational state (e.g., they remain off).

According to an embodiment, the controller module 122 enters either the full operational mode or the no-mobility mode when controller module 122 has received an authentication signal 136, which indicates that an operator with an authorized key has requested that the vehicle be started. More particularly, controller module 122 enters either the full operational mode or the no-mobility operational mode based on the operational mode signal 134 received from vehicle mobility module 124. As mentioned previously, vehicle mobility module 124 indicates, in operational mode signal 134, that the full operational mode is authorized when the signal 132 from impairment sensor system 108 indicates that the IRM meets a criteria (e.g., the blood alcohol concentration is below a predefined threshold). In contrast, vehicle mobility module 124 indicates, in operational mode signal 134, that the no-mobility operational mode is authorized when the signal 132 from impairment sensor system 108 indicates that the IRM does not meet the criteria (e.g., the blood alcohol concentration is above the predefined threshold). When the IRM is blood alcohol concentration, for example, the predefined threshold may be, for example, a value in a range of about 0.02 to about 0.04 percent, although the predefined threshold may be higher or lower, as well.

In the full operational mode, controller module 122 provides control signals 142 to engine/motor 102, which cause engine/motor 102 to start. In addition, controller module 122 may provide control signals 142 to HVAC system 110, which cause HVAC system 110 to control the climate of the interior cab according to operator-adjustable settings. Controller module 122 also may provide control signals 142 to engine/motor 102 and transmission system 112 corresponding to mobility-related actions. For example, the other input devices 114 may include a shift control mechanism, an accelerator pedal, a brake pedal, and a vehicle speed sensor, among other things. When inputs 138 from any of these devices 114 indicate that the vehicle should initiate movement, change a rate of movement, or change a quantity of applied power to the drive train, controller module 122 may provide control signals 142 to the various systems (e.g., engine/motor 102 and transmission system 112, in particular) in order to implement the change. In other words, in the full operational mode, vehicle mobility is permitted and implemented by controller module 122.

In contrast, in the no-mobility operational mode, vehicle mobility is not permitted or implemented by controller module 122. However, cabin conditioning is permitted and implemented by controller module 122, according to an embodiment. In addition, the functionality of one or more other systems 116 not related to mobility also may be permitted and implemented (e.g., an entertainment system, global positioning system (GPS), window actuators, and door lock actuators). Accordingly, in situations in which the impairment sensor system 108 indicates that an IRM does not meet a criteria (e.g., the operator's blood or breath alcohol concentration exceeds the predefined threshold), vehicle mobility is disabled while other vehicle systems are enabled.

For example, HVAC system 110 may be enabled in the no-mobility operational mode. HVAC system 110 includes the radiator and various fans, compressors, condensers, and evaporators, among other things. Operation of some of the HVAC system components may depend on energy supplied by batteries (not illustrated) and engine/motor 102. Accordingly, in an embodiment, engine/motor 102 also may be enabled (e.g., started by controller module 122) in the no-mobility operational mode. However, regardless of the states of other input devices 114, controller module 122 will refrain from providing control signals 142 to engine/motor 102 and transmission system 112 corresponding to mobility-related actions while in the no-mobility operational mode. In addition, certain input devices 114 may be disabled. For example, the vehicle's shift control mechanism (not illustrated) may be locked in a "park" setting, and may be restricted from being moved into gear, according to an embodiment. In addition or alternatively, controller module 122 may disregard operator inputs to the accelerator pedal (not illustrated), and accordingly may refrain from adjusting throttle settings in response to accelerator pedal inputs while in the no-mobility mode.

When inputs 138 from any of the input devices 114 indicate that the vehicle should initiate movement, change a rate of movement, or change a quantity of applied power to the drive train, controller module 122 will refrain from providing control signals 142 to the various systems (e.g., engine/motor 102 and transmission system 112, in particular) in order to implement the change. Alternatively, controller module 122 may provide control signals 142 which otherwise inhibit movement, according to an embodiment. In other words, in the no-mobility operational mode, vehicle mobility is denied and is inhibited by controller module 122.

The system 100 of FIG. 1 may be fully integrated into a vehicle. Accordingly, the various components and functions relating to providing a no-mobility mode may be installed at the factory as original equipment. According to an embodiment, the impairment sensor system 108 may be provided as an option, which may readily be attached or detached from the rest of the system 100, as needed.

Figure 2:
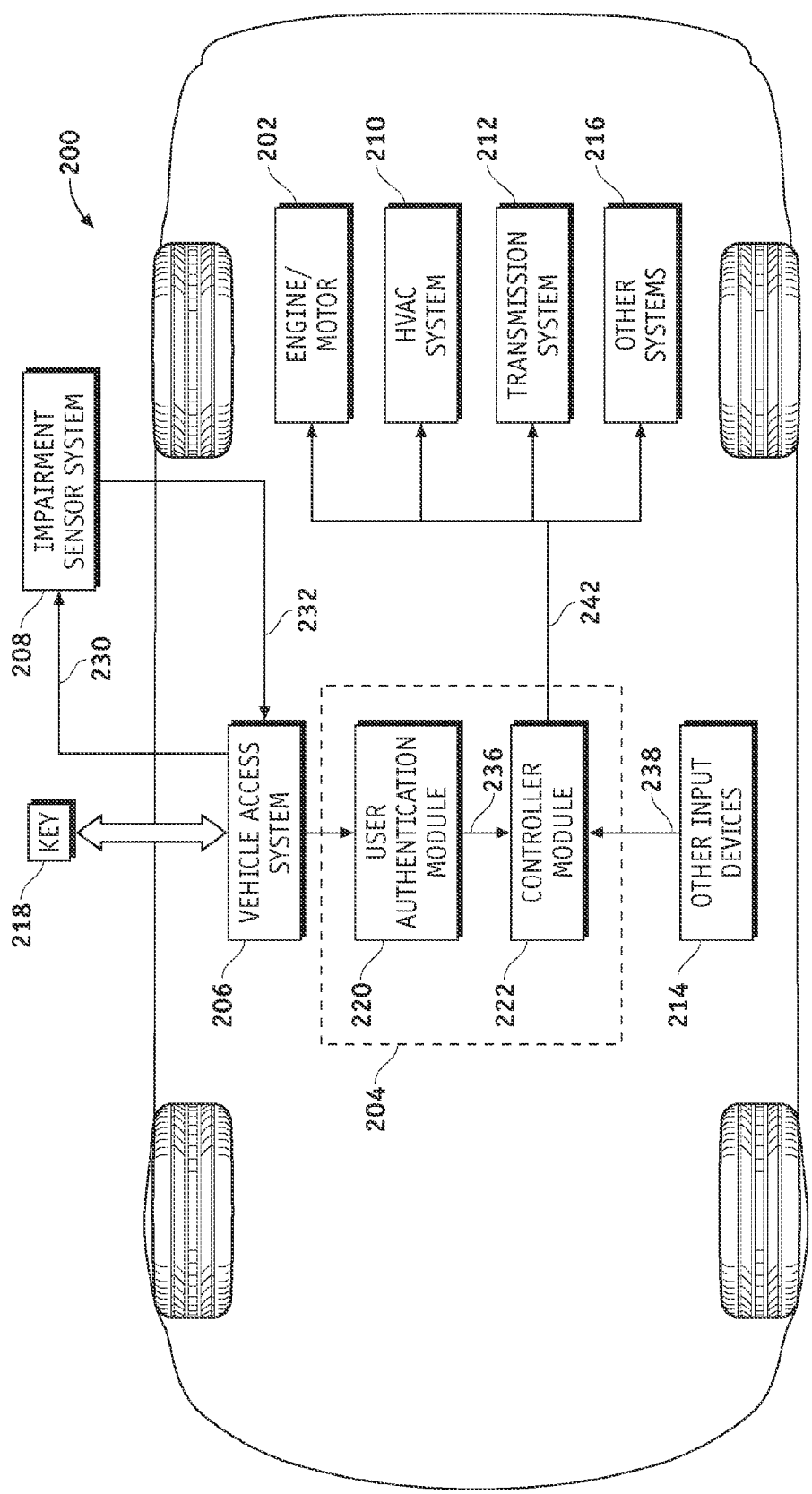
FIG. 2 is a simplified block diagram of a system adapted to control vehicle mobility based on driver impairment determinations, in accordance with an alternate embodiment.

According to another embodiment, some of the previously-described components and/or functionalities relating to providing a no-mobility operational mode may be readily retrofitted to a vehicle as after-market equipment. FIG. 2 is a simplified block diagram of a system 200 adapted to control vehicle mobility based on driver impairment determinations, in accordance with such an alternate embodiment. Although system 200 is described as being capable of being readily retrofitted to a vehicle, it is to be understood that system 200 may be fully integrated into a vehicle at the time of manufacture, as well.

System 200 includes an internal combustion engine and/or electric motor 202 (depending on the type of motor vehicle), processing and control subsystem 204, vehicle access system 206, an impairment sensor system 208, HVAC system 210, and key 218. In a vehicle that includes an internal combustion engine, system 200 also includes a throttle (not illustrated) and transmission system 212. According to various embodiments, system 200 also may include one or more other input devices 214 and/or various other systems 216, as will be discussed in more detail later.

Engine/motor 202, vehicle access system 206, HVAC system 210, transmission system 212, other systems 216, and key 218 may function substantially similarly to the corresponding components described in conjunction with FIG. 1 (e.g., engine/motor 102, vehicle access system 106, HVAC system 110, transmission system 112, other systems 116, and key 118). Accordingly, those components 202, 206, 210, 212, 216, 218 will not be discussed in detail below for the purpose of brevity. However, processing and control subsystem 204, impairment sensor system 208, and some input devices 214 may function substantially differently from the corresponding components described in conjunction with FIG. 1 (e.g., processing and control subsystem 204, impairment sensor system 108, and some input devices 114). Therefore, those components 204, 208, 214 will be discussed in more detail.

Processing and control subsystem 204 may include one or more automotive control modules, electronic control units, general-purpose and/or special-purpose processors, and/or associated electronics. In general, processing and control subsystem 204 is adapted to receive information from various sources (e.g., vehicle access system 206 and other input devices 214), and to control the operation of the vehicle based on the received information. According to an embodiment, processing and control subsystem 204 includes a user authentication module 220 and a controller module 222. Modules 220, 222 may be implemented using separate hardware, or some or all of the modules may be implemented using common hardware. FIG. 2 depicts modules 220, 222 as separate entities for explanation purposes, and not for limitation purposes. User authentication module 220 may function substantially similarly to the corresponding module described in conjunction with FIG. 1 (i.e., user authentication module 120), and therefore it is not discussed in detail here for purposes of brevity.

Similar to the embodiments described in conjunction with FIG. 1, system 200 supports a plurality of operational modes. For example, the operational modes may include modes that are analogous to the "full operational mode", the "no-mobility operational mode", and the "non-operational mode," previously described. However, the full operational mode and the no-mobility operational mode are implemented in substantially different ways, according to the embodiment of FIG. 2.

Controller module 222 implements the full operational mode or the non-operational mode based on signals 236 received from user authentication module 220. Controller module 222 enters or remains in a non-operational mode unless and until controller module 222 receives an authentication signal 236 from user authentication module 220, which indicates that an operator with an authorized key has requested that the vehicle be started. In the non-operational mode, neither the engine/motor 202, the HVAC system 210, the transmission system 212, nor other systems 216 of the vehicle are placed in an operational state (e.g., they remain off). According to an embodiment, the controller module 222 enters the full operational mode when controller module 222 has received an authentication signal 236, which indicates that an operator with an authorized key has requested that the vehicle be started. In the full operational mode, the engine/motor 202, the HVAC system 210, the transmission system 212, and other systems 216 of the vehicle may be placed in an operational state (e.g., they may be turned on). In other words, all of the vehicle subsystems (e.g., engine/motor 202, HVAC system 210, transmission system 212, and other systems 216) are enabled, and the vehicle is capable of being mobilized based on operator inputs.

In the full operational mode, controller module 222 provides control signals 242 to engine/motor 202, which cause engine/motor 202 to start. In addition, controller module 222 may provide control signals 242 to HVAC system 210, which cause HVAC system 210 to control the climate of the interior cab according to operator-adjustable settings. Controller module 222 also may provide control signals 242 to engine/motor 202 and transmission system 212 corresponding to mobility-related actions. For example, the other input devices 214 may include a shift control mechanism, an accelerator pedal, a brake pedal, and a vehicle speed sensor, among other things. When inputs 238 from any of these devices 214 indicate that the vehicle should initiate movement, change a rate of movement, or change a quantity of applied power to the drive train, controller module 222 may provide control signals 242 to the various systems (e.g., engine/motor 202 and transmission system 212, in particular) in order to implement the change. In other words, in the full operational mode, vehicle mobility is permitted and implemented by controller module 222.

In contrast with the embodiments described in conjunction with FIG. 1, impairment sensor system 208 may determine whether the vehicle is to be placed in the no-mobility operational mode. According to an embodiment, the no-mobility operational mode causes the full operational mode to be overridden, as will be explained in more detail below. Impairment sensor system 208 is illustrated outside of the perimeter of the vehicle to indicate that impairment sensor system 208 may include an after-market device that is retrofitted to the vehicle after its original manufacture. Similar to the impairment sensor system described in conjunction with FIG. 1, impairment sensor system 208 may include an analyzer adapted to obtain a sample from the vehicle operator and to determine an IRM from the sample (e.g., to estimate blood alcohol content from a breath sample). According to an embodiment, the analyzer is installed in proximity to the driver's seat of the vehicle (e.g., attached to the dashboard), and is operatively coupled with other components of the system 200, as illustrated in FIG. 2.

Along with the analyzer, impairment sensor system 208 may include a user interface (not illustrated), which is adapted to provide an indication to the vehicle operator when a sample is required. For example, the system 200 may require a sample when the vehicle operator is present in the driver's seat, and attempts to start the engine/motor 202 of the vehicle (e.g., using wireless key 218 or another key). Vehicle access system 206 may provide a signal 230 to impairment sensor system 208 when such an attempt is made. In addition to an initial sample, the system 200 may require additional samples at random times while the vehicle is being driven.

According to an embodiment, impairment sensor system 208 also determines whether or not the vehicle should enter the no-mobility mode. More particularly, the impairment sensor system 208 determines that the vehicle should not enter the no-mobility mode when the impairment sensor system 208 determines that that an IRM determined based on the sample meets a criteria (e.g., a blood alcohol concentration is below a predefined threshold). In contrast, impairment sensor system 208 determines that the vehicle should enter the no-mobility operational mode when the impairment sensor system 208 determines that the IRM does not meet the criteria (e.g., the blood alcohol concentration is above the predefined threshold).

When the impairment sensor system 208 determines that the vehicle should enter the no-mobility operational mode, the impairment sensor system 208 may provide various signals 232 to the vehicle access system 206, to the controller module 222, and/or to various input devices 214, which cause the vehicle access system 206, the controller module 222, and/or the various input devices 214 to disable one or more of the vehicle subsystems associated with vehicle mobility. Alternatively, impairment sensor system 208 may merely include information indicating results of the sample analyses in signals 232. Accordingly, the signals 232 may include, for example, information indicating a result of a sample analysis, an indication that the no-mobility operational mode should be entered, and/or other information that may lead to a determination that one or more of the vehicle subsystems associated with vehicle mobility should be disabled. In other words, the impairment sensor system 208 may cause the vehicle to be immobilized by communicating a signal 232 that results in disabling certain subsystems (e.g., subsystems associated with vehicle mobility), while other subsystems of the vehicle are permitted to operate (e.g., engine/motor 202, HVAC system 210, and other systems 216).

According to an embodiment, in the no-mobility operational mode, signals 232 provided by impairment sensor system 208 to the vehicle access system 206, to the controller module 222, and/or to various input devices 214 may cause certain ones of the input devices 214 to be disabled. For example, according to an embodiment, impairment sensor system 208 may provide signals 232 to vehicle access system 206 (or controller module 222), which may make a determination whether or not to disable an input device 214 based on the information in the signals 232 and other inputs. For example, the vehicle's shift control mechanism (not illustrated) may be locked in a "park" setting, and may be restricted from being moved into gear, according to an embodiment. In addition or alternatively, although signals indicating operator inputs to the accelerator pedal (not illustrated) may be received by controller module 222, controller module 222 may refrain from adjusting throttle settings in response to accelerator pedal inputs if it has also received information (e.g., in signal 232) indicating that the vehicle should be operated in the no-mobility mode.

As with the embodiments of FIG. 1, in the no-mobility operational mode, vehicle mobility is not permitted using the embodiments of FIG. 2. However, cabin conditioning is permitted and implemented by controller module 222, according to an embodiment. In addition, the functionality of one or more other systems 216 not related to mobility also may be permitted and implemented (e.g., entertainment system, GPS, window actuators, and door lock actuators). Accordingly, in situations in which the alcohol concentration sensor system 208 determines that the operator's blood or breath alcohol concentration exceeds the predefined threshold, vehicle mobility is disabled while other vehicle systems are enabled. For example, HVAC system 210, engine/motor 202, and other systems 216 may be enabled in the no-mobility operational mode.

Figure 3:
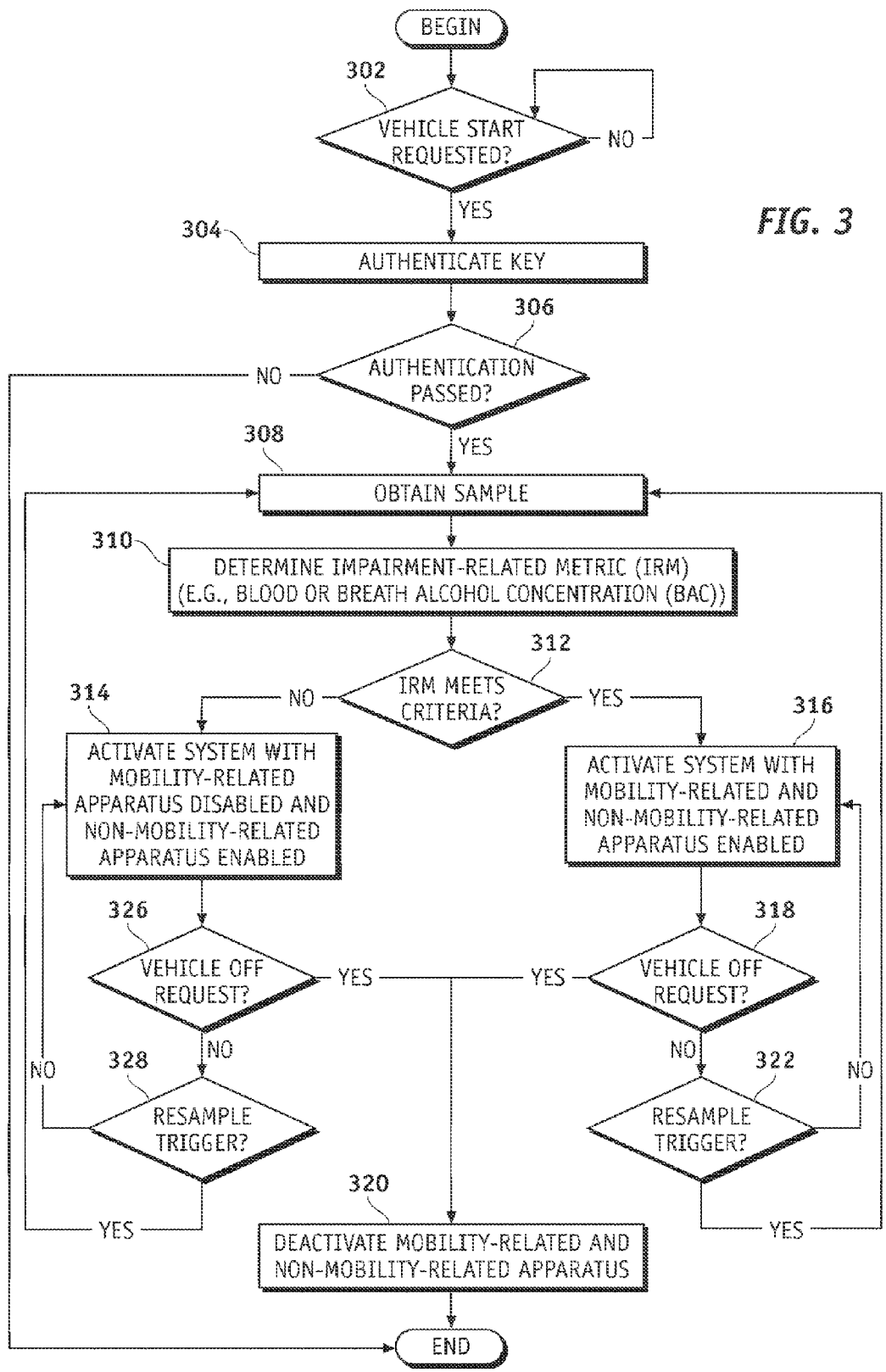
FIG. 3 is a flowchart of a method for controlling vehicle mobility based on driver impairment determinations, in accordance with an embodiment.

FIG. 3 is a flowchart of a method for controlling vehicle mobility based on driver impairment determinations, in accordance with an embodiment. The various method embodiments may be performed, for example, by a system such as system 100 (FIG. 1) or system 200 (FIG. 2). The method may begin, in block 302, when a determination is made whether a request to start the vehicle has been received. For example, the request may comprise a signal from a key (e.g., wireless key 118, 218, FIGS. 1 and 2), which includes an encrypted digital code and an encoded command (e.g., "start vehicle"). Until such a request is made, the method may continue to monitor for a start request, as shown. Upon receiving a vehicle start request, an authenticate key process may be performed in block 304. According to an embodiment, the authenticate key process may include decrypting the digital code, and determining whether the decrypted digital code corresponds to an authorized key. In an alternate embodiment, the vehicle start request (i.e., block 302) and the authentication process (i.e., block 304) may comprise an act, by an operator of the vehicle, of inserting a mechanical key into a key receptacle, and turning the key, thus initiating an ignition signal.

In block 306, a determination is made whether the authenticate key process passed (i.e., an authorized key made the request for vehicle start). If not, then the method ends. According to an embodiment, a vehicle access system (e.g., vehicle access system 106, 206, FIGS. 1 and 2) may be adapted to provide a remote start option, in which the operator may cause the vehicle to be started when the operator is not present in the vehicle. Accordingly, the system also may determine whether or not the operator is present in the vehicle, for example, based on inputs received from a weight sensor in the driver seat. When the weight sensor indicates that a weight above a given threshold is present in the driver's seat, the operator may be determined to be present in the vehicle. Otherwise, the operator may be determined not to be present in the vehicle. Other methods of determining whether or not the operator is present may be utilized in other embodiments.

When a determination is made that the authenticate key process passed and the operator is present in the vehicle, then a sample (e.g., a breath sample) is obtained from the operator, in block 308. According to an embodiment, an impairment sensor system (e.g., impairment sensor system 108, 208, FIGS. 1 and 2) may initiate the process of obtaining a sample by providing a prompt to the user (e.g., in response to a signal from vehicle access system 106, 206, FIGS. 1 and 2).

Upon receiving the sample, the impairment sensor system analyzes the sample to determine an IRM (e.g., a blood alcohol concentration), in block 310, according to an embodiment. As discussed previously, an IRM may include one or more metrics selected from a group of metrics that include a blood alcohol concentration, a breath alcohol concentration, eye nystagmus, blink rate, and/or accuracy in answering questions, performing logical tasks or performing physical tasks, among other things. A determination is then made, in block 312, whether the IRM meets a criteria (e.g., a blood alcohol concentration is less than a predefined threshold).

When the IRM meets the criteria, then the system is activated with one or more mobility-related apparatus enabled and with one or more non-mobility-related apparatus also enabled, in block 316. Accordingly, the vehicle may be in a full operational mode in which the vehicle may be mobilized based on operator inputs (e.g., shifting to drive, depressing the accelerator pedal, and so on). Once the one or more mobility-related and non-mobility-related apparatus have been enabled, a determination may be made, in block 318, whether a request has been made to turn the vehicle off. For example, the vehicle may remain in the full operational mode for the remainder of the drive cycle, and a request to turn off the vehicle may include the operator removing the key from the ignition or pressing a "stop" control. When a request has been made to turn the vehicle off, then in block 320, the one or more mobility-related and non-mobility-related apparatus are deactivated, and the method ends. Deactivation of the one or more mobility-related and non-mobility-related apparatus corresponds to a state transition to a non-operational mode, as will be explained in more detail in conjunction with FIG. 4.

Referring again to block 318, when no request has been made to turn the vehicle off, then a determination may be made, in block 322, whether a resample trigger has occurred. A resample trigger may include, for example, a determination that a resampling time period has expired (e.g., a time period of five minutes, or some other time period), a determination that the vehicle has traveled a pre-defined distance (e.g., ten miles, or some other distance), a determination that the driver has performed some action (e.g., the driver has placed the vehicle in park and/or attempted to shift the vehicle into drive), or a determination that some other triggering event has occurred. When a determination is made that no resample trigger has occurred, then the system is maintained with both the mobility-related apparatus and the non-mobility-related apparatus enabled (i.e., block 316 continues to be performed). When a determination is made that a resample trigger has occurred, then the method returns to block 308, in which a sample is obtained from the vehicle operator, and the method then continues as illustrated. From this point, the vehicle may either be maintained in the full operational mode (e.g., block 316 continues to be performed) or the vehicle may undergo a state transition to the no-mobility operational mode (e.g., block 314 is performed, as described below).

Referring again to block 312, when the IRM does not meet the criteria (e.g., the blood alcohol concentration is greater than the predefined threshold), then the system is activated with one or more mobility-related apparatus disabled and with one or more non-mobility-related apparatus also enabled, in block 314. Accordingly, the vehicle may be in a no-mobility operational mode in which the vehicle may not be mobilized based on operator inputs. However, some subsystems of the vehicle may be permitted to operate (e.g., engine/motor 202, HVAC system 210, and other systems 216). Once the one or more non-mobility-related apparatus have been enabled (and the one or more mobility related apparatus are disabled), a determination may be made, in block 326, whether a request has been made to turn the vehicle off, as described previously in conjunction with block 318. When a request has been made to turn the vehicle off, then in block 320, the one or more non-mobility-related apparatus are deactivated (the mobility-related apparatus already are disabled), and the method ends.

When no request has been made to turn the vehicle off, then a determination may be made, in block 328, whether a resample trigger has occurred, as described previously in conjunction with block 322. When a determination is made that no resample trigger has occurred, then the system is maintained with the mobility-related apparatus disabled and the non-mobility-related apparatus enabled (i.e., block 314 continues to be performed). When a determination is made that a resample trigger has occurred, then the method returns to block 308, in which a sample is obtained from the vehicle operator, and the method then continues as illustrated. From this point, the vehicle may either be maintained in the no-mobility operational mode (e.g., block 314 continues to be performed) or the vehicle may undergo a state transition to the full operational mode (e.g., block 316).

Figure 4:
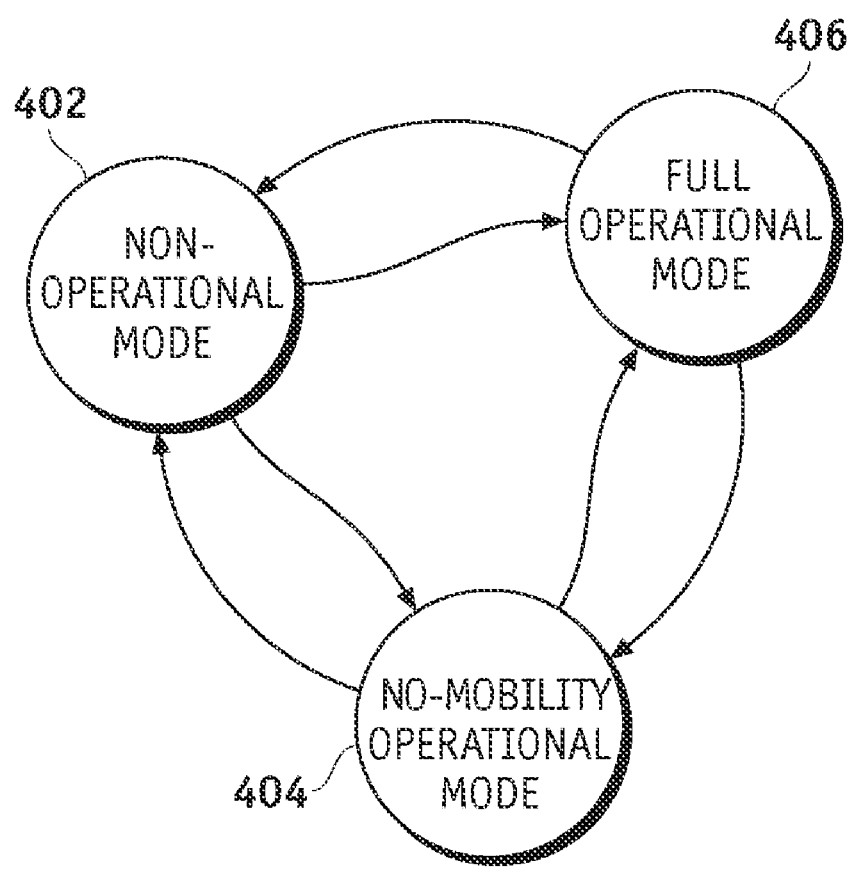
FIG. 4 is a state diagram illustrating various operational modes and transitions between them, in accordance with an embodiment.

FIG. 4 is a state diagram illustrating various operational modes and transitions between them, in accordance with an embodiment. As discussed in detail previously, a vehicle may be in one of three operational modes, according to an embodiment. These operational modes include a non-operational mode 402, a no-mobility operational mode 404, and a full operational mode 406. Initially, when the motor vehicle is turned off, the motor vehicle is in the non-operational mode 402. The vehicle will remain in this mode until some event occurs that causes the vehicle to transition to the no-mobility operational mode 404 or the full operational mode 406.

According to an embodiment, the vehicle may transition out of the non-operational mode 402 to the no-mobility operational mode 404 when the following sequence of events occurs: 1) a vehicle start request is received (e.g., block 302, FIG. 3); 2) a valid key is detected (e.g., blocks 304 and 306, FIG. 3); and 3) the vehicle operator is not present in the vehicle, according to an embodiment. This may correspond to a remote start scenario, for example. Alternatively, the vehicle may transition out of the non-operational mode 302 to the no-mobility operational mode 404 when the following alternative sequence of events occurs: 1) a vehicle start request is received (e.g., block 302, FIG. 3); 2) a valid key is detected (e.g., blocks 304, 306, FIG. 3); 3) the vehicle operator is present in the vehicle; 4) an impairment sensor system has obtained a sample from the vehicle operator and has determined an IRM from the sample (e.g., blocks 308, 310, FIG. 3); and 5) a determination is made that the IRM does not meet a criteria (e.g., block 312, FIG. 3). This may correspond to a scenario in which the vehicle operator has attempted to start the vehicle, but the system has determined that the operator is too impaired to drive. According to an embodiment, the system may periodically or occasionally prompt the vehicle operator for another sample.

According to an embodiment, the system may transition from the no-mobility mode 404 back to the non-operational mode 402 under one or more circumstances. For example, the system may transition from the no-mobility operational mode 404 to the non-operational mode 402 when: 1) a pre-defined time period has been exceeded (e.g., 30 minutes or some other time period); 2) the vehicle operator has provided a user input indicating that the operator wants the vehicle to shut off (e.g., the operator removes the key or leaves the vehicle); or 3) a monitored system parameter (e.g., oil pressure, coolant temperature, fuel level, throttle position, emission fault present, transmission gear selection, and so on) compares unfavorably to a pre-defined limit.

According to an embodiment, while in the no-mobility operational mode 404, the system may periodically or occasionally prompt the vehicle operator for another sample. In such an embodiment, the system may transition from the no-mobility operational mode 404 to the full operational mode 406 when 1) the impairment sensor system has obtained a new sample from the vehicle operator and has determined an IRM from the new sample (e.g., blocks 308, 310, FIG. 3); and 2) a determination is made that the IRM meets a criteria (e.g., block 312, FIG. 3).

Referring again to the non-operational mode 402, the vehicle may transition out of the non-operational mode 402 to the full operational mode 406 when the following sequence of events occurs: 1) a vehicle start request is received (e.g., block 302, FIG. 3); 2) a valid key is detected (e.g., blocks 304, 306, FIG. 3); 3) the vehicle operator is present in the vehicle; 4) an impairment sensor system has obtained a sample from the vehicle operator and has determined an IRM from the sample (e.g., blocks 308, 310, FIG. 3); and 5) a determination is made that the IRM meets a criteria (e.g., block 312, FIG. 3). This may correspond to a scenario in which the vehicle operator has attempted to start the vehicle, and the system has determined that the operator is not too impaired to drive.

According to an embodiment, the system may transition from the full operational mode 406 back to the non-operational mode 402 under one or more circumstances. For example, the system may transition from the full operational mode 406 to the non-operational mode 402 when: 1) the vehicle operator has provided a user input indicating that the operator wants the vehicle to shut off (e.g., the operator removes the key or leaves the vehicle); or 2) a monitored system parameter compares unfavorably to a pre-defined limit, as described above.

As discussed previously, and according to an embodiment, while in the full operational mode 406, the system may periodically or occasionally prompt the vehicle operator for another sample. In such an embodiment, the system may transition from the full operational mode 406 to the no-mobility operational mode 404 when 1) the impairment sensor system has obtained a new sample from the vehicle operator and has determined an IRM from the new sample (e.g., blocks 308, 310, FIG. 3); and 2) a determination is made that the IRM does not meet a criteria (e.g., block 312, FIG. 3). According to an embodiment, when transitioning from the full operational mode 406 to the no-mobility operational mode 404, the system may provide audible and/or visual alarms to alert the vehicle operator that he or she should pull over and park the vehicle, if it is not already parked. At that time (e.g., when the vehicle is safely parked), the vehicle may transition to the no-mobility operational mode 404.

The foregoing description refers to system components, elements, nodes or features being "coupled" or "operatively coupled" together. As used herein, unless expressly stated otherwise, the terms "coupled" and "operatively coupled" mean that one component/element/node/feature is directly or indirectly joined to (or directly or indirectly communicates with) another component/element/node/feature, and not necessarily mechanically. Thus, although the Figures described herein may depict various exemplary arrangements of components/elements/nodes/features, additional intervening components, elements, nodes, features or devices may be present in other embodiments of the depicted subject matter.

While various embodiments of systems and methods have been presented in the foregoing detailed description, it should be appreciated that a vast number of other variations exist. It should also be appreciated that the exemplary embodiment or exemplary embodiments are only examples, and are not intended to limit the scope, applicability, or configuration of the inventive subject matter in any way. Rather, the foregoing detailed description will provide those skilled in the art with a convenient road map for implementing the exemplary embodiment or exemplary embodiments. It should be understood that various changes can be made in the function and arrangement of elements without departing from the scope of the inventive subject matter as set forth in the appended claims and the legal equivalents thereof.

What is claimed is:

1. A system comprising:
an impairment sensor system adapted to perform an analysis of a sample provided by an operator of a motor vehicle, wherein the analysis includes determining an impairment-related metric based on the sample; and
a control subsystem, operatively coupled with the impairment sensor system, and adapted to control at least one mobility-related apparatus and at least one non-mobility-related apparatus of the motor vehicle, wherein, in response to a result of the analysis indicating that the impairment-related metric does not meet a criteria thus indicating that the operator is impaired, the control subsystem transitions to a no-mobility operational mode from a different operational mode, wherein transitioning to the no-mobility operational mode includes the control subsystem disabling the motor vehicle from moving through control of the at least one mobility-related apparatus, and simultaneously allowing the at least one non-mobility-related apparatus to operate through control of the at least one non-mobility-related apparatus, and wherein the different operational mode is chosen from a non-operational mode and a full operational mode, wherein the non-operational mode is an operational mode in which an engine of the motor vehicle is off, and wherein the full operational mode is an operational mode in which the engine is enabled and the motor vehicle is capable of being mobilized.

2. The system of claim 1, wherein the at least one mobility-related apparatus comprises:
a shift control mechanism of the motor vehicle, which is controlled by locking the shift control mechanism.

3. The system of claim 1, wherein the at least one mobility-related apparatus comprises:
a transmission system of the motor vehicle.

4. The system of claim 1, wherein the at least one mobility-related apparatus comprises an apparatus selected from a group of apparatus consisting of a throttle, a fuel delivery system, propulsion battery energy, and an electric park brake system.

5. The system of claim 1, wherein the at least one non-mobility-related apparatus comprises a heating, ventilation, and air conditioning system of the motor vehicle.

6. The system of claim 1, wherein the at least one non-mobility-related apparatus comprises an entertainment system of the motor vehicle.

7. The system of claim 1, wherein the at least one non-mobility-related apparatus comprises the engine of the motor vehicle.

8. The system of claim 1, wherein the sample includes a breath sample, wherein the analysis includes an analysis of the sample to determine the impairment-related metric as a blood alcohol concentration, wherein the result indicates the blood alcohol concentration, and wherein the control subsystem controls the at least one mobility-related apparatus in the manner that disables the motor vehicle when the blood alcohol concentration is above a threshold.

9. A system comprising:
an impairment sensor system adapted to perform an analysis of a sample provided by an operator of a motor vehicle, wherein the analysis includes determining an impairment-related metric based on the sample, and wherein the impairment sensor system is further adapted to provide a signal in response to the impairment sensor system detecting that the impairment-related metric does not meet a criteria and thus that the operator is impaired, wherein the signal causes the motor vehicle to transition to a no-mobility operational mode from a different operational mode, wherein transitioning to the no-mobility operational mode includes disabling the motor vehicle from moving through control of at least one mobility-related apparatus of the motor vehicle, and allowing at least one non-mobility-related apparatus of the motor vehicle to operate through control of the at least one non-mobility related apparatus, and wherein the different operational mode is chosen from a non-operational mode and a full operational mode, wherein the non-operational mode is an operational mode in which an engine of the motor vehicle is off, and wherein the full operational mode is an operational mode in which the engine is enabled and the motor vehicle is capable of being mobilized.

10. The system of claim 9, wherein the at least one mobility-related apparatus comprises:
a shift control mechanism of the motor vehicle, which is disabled by locking the shift control mechanism.

11. The system of claim 9, wherein the at least one mobility-related apparatus comprises:
a transmission system of the motor vehicle.

12. The system of claim 9, wherein the at least one mobility-related apparatus comprises an apparatus selected from a group of apparatus consisting of a throttle, a fuel delivery system, propulsion battery energy, and an electric park brake system.

13. The system of claim 9, wherein the at least one non-mobility-related apparatus comprises a heating, ventilation, and air conditioning system of the motor vehicle.

14. The system of claim 9, wherein the at least one non-mobility-related apparatus comprises an entertainment system of the motor vehicle.

15. The system of claim 9, wherein the non-mobility-related apparatus comprises the engine of the motor vehicle.

16. The system of claim 9, wherein the impairment-related metric includes a blood alcohol concentration.

17. A method for immobilizing a motor vehicle, the method comprising the steps of:
determining an impairment-related metric from a sample obtained from a vehicle operator;
determining whether the impairment-related metric meets a criteria; and
in response to the impairment-related metric not meeting the criteria thus indicating that the vehicle operator is impaired, transitioning to a no-mobility operational mode from a different operational mode, wherein transitioning to the no-mobility operational mode includes disabling at least one mobility-related apparatus of the motor vehicle in order to disable the motor vehicle from moving, and allowing at least one non-mobility-related apparatus of the motor vehicle to be enabled, and wherein the different operational mode is chosen from a non-operational mode and a full operational mode, wherein the non-operational mode is an operational mode in which an engine of the motor vehicle is off, and wherein the full operational mode is an operational mode in which the engine is enabled and the motor vehicle is capable of being mobilized.

18. The method of claim 17, wherein transitioning to the no-mobility operational mode comprises:
locking a shift control mechanism of the motor vehicle.

19. The method of claim 17, wherein transitioning to the no-mobility operational mode comprises:
disabling a transmission system of the motor vehicle.

20. The method of claim 17, wherein transitioning to the no-mobility operational mode comprises:
refraining from disabling a heating, ventilation, and air conditioning system of the motor vehicle.

* * * * *